United States Patent
Randhawa et al.

(10) Patent No.: US 12,232,482 B2
(45) Date of Patent: Feb. 25, 2025

(54) HYBRID TOMATO VARIETY 'VT19077601'

(71) Applicant: Axia Vegetable Seeds Group, Inc., Woodland, CA (US)

(72) Inventors: Lakhwinder Randhawa, Woodland, CA (US); Mario Velasco Alvarado, Culiacan (MX); Higinio Mayorquin, Culiacan (MX)

(73) Assignee: Axia Vegetable Seeds Group, Inc., Woodland, CA (US)

( * ) Notice: Subject to any disclaimer, the term of this patent is extended or adjusted under 35 U.S.C. 154(b) by 138 days.

(21) Appl. No.: 17/709,057

(22) Filed: Mar. 30, 2022

(65) Prior Publication Data

US 2022/0322629 A1    Oct. 13, 2022

Related U.S. Application Data

(60) Provisional application No. 63/169,620, filed on Apr. 1, 2021.

(51) Int. Cl.
*A01H 6/82*    (2018.01)
*A01H 5/08*    (2018.01)
*A01H 5/10*    (2018.01)

(52) U.S. Cl.
CPC .............. *A01H 6/825* (2018.05); *A01H 5/08* (2013.01); *A01H 5/10* (2013.01)

(58) Field of Classification Search
None
See application file for complete search history.

(56) References Cited

U.S. PATENT DOCUMENTS

| | | |
|---|---|---|
| 8,946,506 B2 | 2/2015 | Maris et al. |
| 11,344,002 B1 * | 5/2022 | Kuehn ................... A01H 6/825 |
| 2011/0209240 A1 | 8/2011 | Heath |
| 2022/0354081 A1 | 11/2022 | Randhawa et al. |

* cited by examiner

*Primary Examiner* — Weihua Fan
*Assistant Examiner* — Brian James Sullivan
(74) *Attorney, Agent, or Firm* — Morrison & Foerster LLP

(57) ABSTRACT

Hybrid tomato variety designated 'VT19077601' is disclosed. 'VT19077601' is a hybrid tomato variety exhibiting stability and uniformity.

16 Claims, 4 Drawing Sheets

(4 of 4 Drawing Sheet(s) Filed in Color)

HYBRID TOMATO VARIETY 'VT19077601'

CROSS-REFERENCE TO RELATED APPLICATION

This application claims the benefit of U.S. Provisional Application No. 63/169,620, filed Apr. 1, 2021, which is hereby incorporated by reference in its entirety.

FIELD

The present disclosure relates to the field of plant breeding. In particular, the present disclosure relates to new and distinctive tomato, Solanum lycopersicum, hybrid varieties designated 'VT19077601' and 'VT19077602'.

BACKGROUND

Cultivated and commercial forms of tomato belong to the large and diverse genus Solanum, which also includes many other flowering plants such as nightshades, potato, and eggplant. It is believed that the tomato species, Solanum lycopersicum, originated in the Americas, being native to Ecuador, Peru and the Galapagos Islands, and was initially cultivated by Aztecs and Incas as early as 700 AD. Mexico appears to have been the site of domestication and the source of the earliest introduction. It is thought that the cherry tomato, S. lycopersicum var. cerasiforme, is the direct ancestor of modern cultivated forms.

As a crop, tomato is grown for its fruit, which is widely used as a fresh market or processed product. The size of tomato fruits may range from small to large, and there are cherry, plum, pear, standard, and beefsteak types. Tomato is grown commercially wherever environmental conditions permit the production of an economically viable yield. For example, in the United States, over 500,000 acres of tomatoes are grown annually, with approximately 40% of tomatoes being grown for fresh market consumption and the rest for processing. The largest market for processing tomatoes in the United States is in California, where processing tomatoes are harvested by machine. California is also the second largest fresh market for tomatoes, the majority of which are harvested by hand at vine ripe and mature green stages of ripeness. Fresh market tomatoes are available in the United States year round. Processing tomato season in California is from late June to September.

S. lycopersicum is a simple diploid species with twelve pairs of differentiated chromosomes. The cultivated tomato is self-fertile and almost exclusively self-pollinating. The tomato flowers are hermaphrodites. Commercial cultivars were initially open-pollinated, but most have now been replaced by better yielding hybrids. Due to its wide dissemination and high value, tomato has been intensively bred.

Tomatoes may be grouped by the amount of time it takes for the plants to mature fruit for harvest; in general the cultivars are classified as early, midseason, or late-maturing. Tomatoes can also be grouped by the plant's growth habit, which can be determinate or indeterminate. Determinate plants tend to grow their foliage first, then set flowers that mature into fruit if pollination is successful. All of the fruit tend to ripen on a plant at about the same time. Indeterminate tomatoes start out by growing some foliage, then continue to produce foliage and flowers throughout the growing season. These plants tend to have tomato fruit in different stages of maturity at any given time. Additionally, tomatoes can be grouped by shape (e.g., plum or saladette, round, beef, specialty, etc.). Recent developments in tomato breeding have led to a wider array of fruit color; in addition to the standard red ripe color, tomatoes can be creamy white, lime green, pink, yellow, golden, or orange.

Tomato is an important and valuable field crop. Thus, there is a continued need for new tomato varieties. In particular, there is a need for improved tomato varieties that are stable, high yielding, and agronomically sound.

BRIEF SUMMARY

In order to meet these needs, the present disclosure is directed to improved hybrid tomato varieties.

In one aspect, the present disclosure is directed to a hybrid tomato, Solanum lycopersicum, seed designated as 'VT19077601', representative sample of seed having been deposited under ATCC Accession Number PTA-127760. In one embodiment, the present disclosure is directed to a Solanum lycopersicum tomato plant and parts isolated therefrom produced by growing 'VT19077601' tomato seed. In another embodiment, the present disclosure is directed to a Solanum lycopersicum plant and parts isolated therefrom having all the physiological and morphological characteristics of a Solanum lycopersicum plant produced by growing 'VT19077601' tomato seed having ATCC Accession Number PTA-127760. In still another embodiment of this aspect, the present disclosure is directed to a method of making tomato seeds, the method comprising crossing a 'VT19077601' tomato plant with another tomato plant and harvesting seed therefrom.

Tomato plant parts include tomato leaves, ovules, pollen (pollen grains), seeds, tomato fruits, parts of tomato fruits, flowers, cells, and the like. In one embodiment, the present disclosure is directed to a tomato leaf, an ovule, a pollen grain, a fruit, or a cell isolated from 'VT19077601' tomato plants. In certain embodiments, the present disclosure is further directed to pollen or ovules isolated from 'VT19077601' tomato plants. In another embodiment, the present disclosure is further directed to protoplasts produced from 'VT19077601' tomato plants. In another embodiment, the present disclosure is further directed to tissue or cell culture of 'VT19077601' tomato plants, and to tomato plants regenerated from the tissue or cell culture, where the plant has all of the morphological and physiological characteristics of 'VT19077601' tomato. In certain embodiments, tissue or cell culture of 'VT19077601' tomato plants is produced from a plant part selected from root, root tip, meristematic cell, stem, hypocotyl, petiole, cotyledon, leaf, flower, anther, pollen, pistil, and fruit.

In a further aspect, the present disclosure is directed to a method of producing a seed of a 'VT19077601'-derived tomato plant, including the steps of: (a) crossing a hybrid tomato designated as 'VT19077601', representative sample of seed having been deposited under ATCC Accession Number PTA-127760, with itself or a second tomato plant; and (b) allowing seed of a 'VT19077601'-derived tomato plant to form. In another embodiment of this aspect, the method further includes the steps of: (c) crossing a plant grown from 'VT19077601'-derived tomato seed with itself or a second tomato plant to yield additional 'VT19077601'-derived tomato seed; (d) growing the additional 'VT19077601'-derived tomato seed of step (c) to yield additional 'VT19077601'-derived tomato plants; and (e) repeating steps (c) and (c) for an additional 3-10 generations to generate further 'VT19077601'-derived tomato plants.

In yet another aspect, the present disclosure is directed to a method of vegetatively propagating a plant of hybrid tomato 'VT19077601', the method including the steps of:

(a) collecting tissue capable of being propagated from a plant of hybrid tomato 'VT19077601', representative sample of seed having been deposited under ATCC Accession Number PTA-127760; (b) cultivating the tissue to obtain proliferated shoots; and (c) rooting the proliferated shoots to obtain rooted plantlets. In a further embodiment of this aspect, the method further includes step (d) growing plants from the rooted plantlets.

In one aspect, the present disclosure is directed to a hybrid tomato, *Solanum lycopersicum*, seed designated as 'VT19077602', representative sample of seed having been deposited under ATCC Accession Number X2. In one embodiment, the present disclosure is directed to a *Solanum lycopersicum* tomato plant and parts isolated therefrom produced by growing 'VT19077602' tomato seed. In another embodiment, the present disclosure is directed to a *Solanum lycopersicum* plant and parts isolated therefrom having all the physiological and morphological characteristics of a *Solanum lycopersicum* plant produced by growing 'VT19077602' tomato seed having ATCC Accession Number X2. In still another embodiment of this aspect, the present disclosure is directed to a method of making tomato seeds, the method comprising crossing a 'VT19077602' tomato plant with another tomato plant and harvesting seed therefrom.

Tomato plant parts include tomato leaves, ovules, pollen (pollen grains), seeds, tomato fruits, parts of tomato fruits, flowers, cells, and the like. In one embodiment, the present disclosure is directed to a tomato leaf, an ovule, a pollen grain, a fruit, or a cell isolated from 'VT19077602' tomato plants. In certain embodiments, the present disclosure is further directed to pollen or ovules isolated from 'VT19077602' tomato plants. In another embodiment, the present disclosure is further directed to protoplasts produced from 'VT19077602' tomato plants. In another embodiment, the present disclosure is further directed to tissue or cell culture of 'VT19077602' tomato plants, and to tomato plants regenerated from the tissue or cell culture, where the plant has all of the morphological and physiological characteristics of 'VT19077602' tomato. In certain embodiments, tissue or cell culture of 'VT19077602' tomato plants is produced from a plant part selected from root, root tip, meristematic cell, stem, hypocotyl, petiole, cotyledon, leaf, flower, anther, pollen, pistil, and fruit.

In a further aspect, the present disclosure is directed to a method of producing a seed of a 'VT19077602'-derived tomato plant, including the steps of: (a) crossing a hybrid tomato designated as 'VT19077602', representative sample of seed having been deposited under ATCC Accession Number X2, with itself or a second tomato plant; and (b) allowing seed of a 'VT19077602'-derived tomato plant to form. In another embodiment of this aspect, the method further includes the steps of: (c) crossing a plant grown from 'VT19077602'-derived tomato seed with itself or a second tomato plant to yield additional 'VT19077602'-derived tomato seed; (d) growing the additional 'VT19077602'-derived tomato seed of step (c) to yield additional 'VT19077602'-derived tomato plants; and (e) repeating steps (c) and (c) for an additional 3-10 generations to generate further 'VT19077602'-derived tomato plants.

In yet another aspect, the present disclosure is directed to a method of vegetatively propagating a plant of hybrid tomato 'VT19077602', the method including the steps of: (a) collecting tissue capable of being propagated from a plant of hybrid tomato 'VT19077602', representative sample of seed having been deposited under ATCC Accession Number X2; (b) cultivating the tissue to obtain proliferated shoots; and (c) rooting the proliferated shoots to obtain rooted plantlets. In a further embodiment of this aspect, the method further includes step (d) growing plants from the rooted plantlets.

In another embodiment, the present disclosure is further directed to tomato plants, plant parts and seeds produced by the tomato plants where the tomato plants are produced by any of the preceding methods of the disclosure.

In addition to the exemplary aspects and embodiments described above, further aspects and embodiments will become apparent by study of the following descriptions.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1A shows plants and fruit of hybrid tomato 'VT19077601'. FIG. 1B shows mature and immature fruit of hybrid tomato 'VT19077601'. FIG. 1C shows side views, a cross-section, and a peduncle end of fruit as well as a leaf of hybrid tomato 'VT19077601'.

FIG. 2A shows plants and fruit of hybrid tomato 'VT19077602'. FIG. 2B shows mature and immature fruit of hybrid tomato 'VT19077602'. FIG. 2C shows side views, a cross-section, and a peduncle end of fruit as well as a leaf of hybrid tomato 'VT19077602'.

DETAILED DESCRIPTION

Figure 1A:
FIGS. 1A-1C show plant, fruit, and leaf of hybrid tomato 'VT19077601'.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The selected germplasm is crossed in order to recombine the desired traits and, through selection, varieties or parent lines are developed. The goal is to combine, in a single variety or hybrid, an improved combination of desirable traits from the parental germplasm. These important traits may include higher yield, field performance, fruit and agronomic quality such as firmness, color, content in soluble solids, acidity and viscosity, resistance to diseases and insects, and tolerance to drought and heat. As tomato fruits may be subject to mechanical harvesting for processing purposes, i.e., juice, paste, catsup, etc., uniformity of plant characteristics such as germination, growth rate, maturity and plant uniformity is also desirable.

Choice of breeding or selection methods can depend on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences the choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the case of pollination, the frequency of successful hybrids from pollinations, and the number of hybrid offspring from each successful cross.

Each breeding program may include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for at least three years. The best lines can then be candidates for new commercial cultivars. Those still deficient in a few traits may be used as parents to produce new populations for further selection. These processes, which lead to the final step of marketing and distribution, may take from eight to twelve years from the time the first cross or selection is made.

One goal of tomato breeding is to develop new, unique, and genetically superior tomato inbred lines and hybrids. A breeder can initially select and cross two or more parental lines, followed by repeated selfing and selection, producing many new genetic combinations. A plant breeder can then select which germplasms to advance to the next generation. These germplasms may then be grown under different geographical, climatic, and soil conditions, and further selections can be made during, and at the end of, the growing season. In the case of hybrid variety development, two parental lines may be crossed to produce $F_1$ progeny. A single-cross hybrid is produced when two inbred lines are crossed to produce an $F_1$ hybrid. Once the parental lines that give the best hybrid performance have been identified, the hybrid seed can be reproduced indefinitely as long as the homogeneity of the inbred parent is maintained. Alternatively, a hybrid tomato plant may also serve as a parent in the development of another hybrid tomato plant.

The development of commercial tomato varieties thus requires the development of tomato parental lines, the crossing of these lines, and the evaluation of the crosses. Various breeding methods may be used to develop tomato varieties from breeding populations and non-limiting examples of such methods are described herein. Breeding programs can be used to combine desirable traits from two or more varieties or various broad-based sources into breeding pools from which lines are developed by selfing and selection of desired phenotypes. The new lines are crossed with other lines and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, DNA- or RNA-sequencing, CAPS Markers, ELISA, Western blot, microarrays, Single Nucleotide Polymorphisms (SNPs), Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), Differential Display Polymerase Chain Reaction (DD-PCR), Quantitative Real-Time Polymerase Chain Reaction (qRT-PCR), DNA Amplification Fingerprinting (DAF), Sequence Characterized Amplified Regions (SCARs), Amplified Fragment Length Polymorphisms (AFLPs), and Simple Sequence Repeats (SSRs, which are also referred to as Microsatellites).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection.

Molecular markers may also be used to identify and exclude certain sources of germplasm as parental varieties or ancestors of a plant by providing a means of tracking genetic profiles through crosses.

Mutation breeding may also be used to introduce new traits into tomato varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Additional non-limiting examples of breeding methods that may be used include, without limitation, those found in *Principles of Plant Breeding*, John Wiley and Son, pp. 115-161 (1960); Allard (1960); Simmonds (1979); Sneep, et al. (1979); and Fehr (1987).

Definitions

In the description and tables that follow, a number of terms are used. In order to provide a clear and consistent understanding of the specification and claims, the following definitions are provided.

Allele. An allele is any of one or more alternative form of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

BRIX. Means a percentage by weight of the sugar in solution (e.g., from a fruit) measured using a refractometer, wherein the fruit is cut in half and the juice within the fruit is squeezed onto a lens. The juice on the lens is then measured by the refractometer.

Determinate tomato. A variety that comes to fruit all at once, then stops bearing. Determinate varieties are best suited for commercial growing since they can be harvested all at once.

Essentially all the physiological and morphological characteristics. A plant having essentially all the physiological and morphological characteristics of another plant means a plant having the physiological and morphological characteristics, except for the characteristics derived from the converted gene, of the other plant.

Flesh color. The color of the tomato flesh that can range from orange-red to dark red when at ripe stage (harvest maturity).

Fruit. A ripened ovary, together with any other structures that ripen with the ovary and form a unit.

Indeterminate tomato. A variety that continues to set and ripen fruit throughout the season.

Plant part. A plant part means any part of a plant including, for example, a cell, protoplast, embryo, pollen grain, ovule, flower, leaf, stem, cotyledon, hypocotyl, meristematic cell, rootstock, root, root tip, pistil, anther, shoot tip, shoot, fruit and petiole.

Regeneration. Regeneration refers to the development of a plant from tissue culture.

Relative maturity. Relative maturity is an indication of time until a tomato genotype is ready for harvest. A genotype is ready for harvest when 90% or more of the tomatoes are ripe.

Semi-erect habit. A semi-erect plant has a combination of lateral and upright branching and has an intermediate-type habit between a prostate plant habit, having laterally growing branching with fruits most of the time on the ground, and an erect plant habit, having branching going straight up with fruit being off the ground.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Soluble Solids. Soluble solids refer to the percent of solid material found in the fruit tissue, the vast majority of which is sugars. Soluble solids are directly related to the finished processed product yield of pastes and sauces. Soluble solids are estimated with a refractometer, and measured as degrees brix.

Quantitative Trait Loci (QTL). Quantitative trait loci refer to genetic loci that control to some degree numerically representable traits that are usually continuously distributed.

Uniform ripening. Refers to a tomato that ripens uniformly, i.e., one that has no green discoloration on the shoulders. The uniform ripening is controlled by a single recessive gene.

Vegetative propagation. Refers to taking part of a plant and allowing that plant part to form roots where plant part is defined as leaf, pollen, embryo, cotyledon, hypocotyl, meristematic cell, root, root tip, pistil, anther, flower, shoot tip, shoot, stem, fruit and petiole.

Vigor. Plant vigor is scored on a scale of 1 to 9, with 1 being very weak and 9 being very strong.

Overview of Hybrid Tomato 'VT19077601'

Figure 1B:
Figure 1C:

Hybrid tomato 'VT19077601' is seed propagated, has indeterminate growth, and produces obovate fruits weighing 110-140 g. Hybrid tomato 'VT19077601' is adapted for protected cultivation conditions like greenhouse or mesh house. In addition, hybrid tomato 'VT19077601' is highly resistant to *Fusarium* wilt (*Fusarium oxysporum* f. sp. *lycopersici*) races 1 and 3, Tomato yellow leaf curl virus (TYLCV), Tomato Spotted Wilt Virus (TSWV), *Verticillium* wilt (*Verticillium albo-atrum* and *Verticillium* dahlia), Tomato gray leaf spot (*Stemphylium lycopersici*), Root-knot nematodes *Meloidogyne incognita* (Mi), *Meloidogyne arenaria* (Ma), and *Meloidogyne javanica* (Mj), and Tobacco mosaic virus (TMV); and susceptible to *Fusarium* wilt (*Fusarium oxysporum* f. sp. *lycopersici*) race 2. Hybrid tomato 'VT19077601' is the result of numerous generations of plant selections from its parent lines and good heterotic pattern in the hybrid combination, and was chosen for its plant health, fruit firmness, fruit size, number of fruit per cluster, and disease resistance. FIG. 1A shows plants and fruit of hybrid tomato 'VT19077601'. FIG. 1B shows mature and immature fruit of hybrid tomato 'VT19077601'. FIG. 1C shows side views, a cross-section, and a peduncle end of fruit as well as a leaf of hybrid tomato 'VT19077601'.

Hybrid tomato 'VT19077601' has shown uniformity and stability for the traits, within the limits of environmental influence for the traits. The hybrid has been increased with continued observation for uniformity. No variant traits have been observed or are expected in hybrid tomato 'VT19077601'.

Objective Description of the Hybrid Tomato 'VT19077601'

The terminology and descriptors used in this section are in line with the descriptors of the "UPOV Guidelines for the Conduct of Tests for Distinctness, Uniformity, and Stability", or the "Test Guidelines" for *Solanum lycopersicum*.

The "Test Guidelines" indicate reference varieties for the descriptors or characteristics that are included in the list. The terminology and descriptors used in these tables are in line with the official terminology as of the filing date, and are thus clear for a person skilled in the art.

Hybrid tomato 'VT19077601' has the following morphologic and other characteristics:
Plant:
  Type: Saladette
  Growth type: Indeterminate
  Division of blade: Bipinnate
  Vigor: Strong (Scores 8 on a scale of 1 to 9)
Peduncle:
  Abscission layer: Present
Fruit:
  Size: Large (110-140 g)
  Shape in longitudinal section: Obovate
  Ribbing at peduncle end: Absent or very weak
  Pointed shape at blossom end: Absent
  Number of locules: Two or three
  Green shoulder (before maturity): Absent
  Color at maturity: Red
  Firmness: Very firm
  Number of fruits per cluster: 8-10
Disease and Pest Resistances:
  *Fusarium* wilt (*Fusarium oxysporum* f. sp. *lycopersici*) races 1 and 3: Highly resistant
  *Fusarium* wilt (*Fusarium oxysporum* f. sp. *lycopersici*) race 2: Susceptible
  Tomato yellow leaf curl virus (TYLCV): Highly resistant
  Tomato Spotted Wilt Virus (TSWV): Highly resistant
  *Verticillium* wilt (*Verticillium albo-atrum* and *Verticillium* dahlia): Highly resistant
  Tomato gray leaf spot (*Stemphylium lycopersici*): Highly resistant
  Root-knot nematodes *Meloidogyne incognita* (Mi), *Meloidogyne arenaria* (Ma), and *Meloidogyne javanica* (Mj): Highly resistant

Comparison to Other Tomato Varieties

Table 1 below compares characteristics of hybrid tomato 'VT19077601' with the tomato variety 'Latino' (unpatented). Column 1 lists the characteristics, column 2 shows the characteristics for hybrid tomato 'VT19077601', and column 3 shows the characteristics for tomato variety 'Latino'.

TABLE 1

| Characteristic | 'VT19077601' | 'Latino' |
|---|---|---|
| Fruit shape | Obovate | Rectangular or oval blocky |
| Number of fruit per cluster | 8-10 | 6-8 |
| Fruit firmness | Very firm | Firm |
| Plant health | Very healthy | Healthy |
| *Fusarium* wilt (*Fusarium oxysporum* f. sp. *lycopersici*) race 2 | Susceptible | Resistant |
| Tomato yellow leaf curl virus (TYLCV) | Highly resistant | Susceptible |
| Tomato Spotted Wilt Virus (TSWV) | Highly resistant | Susceptible |
| *Verticillium* wilt (*Verticillium alboatrum* and *Verticillium dahlia*) | Highly resistant | Resistant |
| Tomato gray leaf spot (*Stemphylium lycopersici*) | Highly resistant | Susceptible |
| Root-knot nematodes *Meloidogyne incognita* (Mi), *Meloidogyne arenaria* (Ma), and *Meloidogyne javanica* (Mj) | Highly resistant | Susceptible |
| Tobacco mosaic virus (TMV) | Highly resistant | Susceptible |

Table 2 below compares characteristics of hybrid tomato 'VT19077601' with the tomato varieties 'El Dorado' (unpatented) and 'PaiPai' (unpatented) over two separate trials in one year under greenhouse culture in Hidalgo and San Luis Potosí, Mexico. Column 1 lists the characteristics, columns 2 and 4 show the characteristics for hybrid tomato 'VT19077601', and columns 3 and 5 show the characteristics for tomato varieties 'El Dorado' and 'PaiPai'. Trial numbers, locations, and evaluation times are noted in row 1, above their respective data.

TABLE 2

| Variety | Trial 1: Dolores, Hidalgo Evaluation: May, Year 1 | | Trial 2: El Cedral, S.L.P. Evaluation: August, Year 1 | |
| --- | --- | --- | --- | --- |
| | 'VT19077601' | El Dorado' | 'VT19077601' | 'PaiPai' |
| Days to Harvest | 78 | 78 | — | — |
| Plant Vigor[1] | 3 | 4 | 3 | 4 |
| Disease Pressure[2] | 3 | 4 | 3 | 4 |
| Maturity[3] | Main | Main | Main | Main |
| Yield[4] | 3 | 4 | 3 | 4 |
| Fruit Shape Uniformity[5] | 3 | 4 | 4 | 4 |
| Fruit Size Uniformity[5] | 3 | 4 | 3 | 4 |
| Fruit Size (g) | 120 | 120 | 121.6 | 127 |
| Fruit Size (cm) | 10 × 8 × 0.5 | 9 × 8 × 0.6 | 7 × 6.1 × 1 | 7.8 × 5.9 × 1 |

[1]Plant Vigor (1-5): 1. No stand/germ.; 2. Poor vigor; 3. Average vigor; 4. Good vigor; 5. Excellent vigor.
[2]Disease Pressure (1-5): 1. No stand/germ.; 2. Poor resistance; 3. Average resistance; 4. Good resistance; 5. Excellent resistance.
[3]Maturity: Relative harvest time compared to other tomato varieties. Categories: Early, Main, Late, Transition.
[4]Yield (1-5): 1. No stand/germ.; 2. Poor yield; 3. Average yield; 4. Good yield; 5. Excellent yield.
[5]Fruit uniformity (1-5): 1. No stand/germ.; 2. Poor uniformity; 3. Average uniformity; 4. Good uniformity; 5. Excellent uniformity.

Overview of Hybrid Tomato 'VT19077602'

Figure 2A:
FIGS. 2A-2C show plant, fruit, and leaf of hybrid tomato 'VT19077602'.
Figure 2B:
Figure 2C:

Hybrid tomato 'VT19077602' is seed propagated, has indeterminate growth, and produces obovate fruits weighing 130-150 g. Hybrid tomato 'VT19077602' is adapted for protected cultivation conditions like greenhouse or mesh house. In addition, hybrid tomato 'VT19077602' is highly resistant to Fusarium wilt (Fusarium oxysporum f. sp. lycopersici) races 1, 2, and 3, Tomato yellow leaf curl virus (TYLCV), Tomato Spotted Wilt Virus (TSWV), Verticillium wilt (Verticillium albo-atrum and Verticillium dahlia), Root-knot nematodes Meloidogyne incognita (Mi), Meloidogyne arenaria (Ma), and Meloidogyne javanica (Mj), and Alternaria alternata f. sp. lycopersici (Alternaria stem canker, ASC); and susceptible to Tomato mosaic virus (ToMV). Hybrid tomato 'VT19077602' is the result of numerous generations of plant selections from its parent lines and good heterotic pattern in the hybrid combination, and was chosen for its plant health, fruit shape, fruit firmness, and disease resistance. FIG. 2A shows plants and fruit of hybrid tomato 'VT19077602'. FIG. 2B shows mature and immature fruit of hybrid tomato 'VT19077602'. FIG. 2C shows side views, a cross-section, and a peduncle end of fruit as well as a leaf of hybrid tomato 'VT19077602'.

Hybrid tomato 'VT19077602' has shown uniformity and stability for the traits, within the limits of environmental influence for the traits. The hybrid has been increased with continued observation for uniformity. No variant traits have been observed or are expected in hybrid tomato 'VT19077602'.

Objective Description of the Hybrid Tomato 'VT19077602'

The terminology and descriptors used in this section are in line with the descriptors of the "UPOV Guidelines for the Conduct of Tests for Distinctness, Uniformity, and Stability", or the "Test Guidelines" for Solanum lycopersicum. The "Test Guidelines" indicate reference varieties for the descriptors or characteristics that are included in the list. The terminology and descriptors used in these tables are in line with the official terminology as of the filing date, and are thus clear for a person skilled in the art.

Hybrid tomato 'VT19077602' has the following morphologic and other characteristics:
Plant:
  Type: Saladette
  Growth type: Indeterminate
  Division of blade: Bipinnate
  Vigor: Strong (Scores 8 on a scale of 1 to 9)
Peduncle:
  Abscission layer: Present
Fruit:
  Size: Mostly large (130-150 g)
  Shape in longitudinal section: Obovate
  Ribbing at peduncle end: Absent or very weak
  Pointed shape at blossom end: Absent
  Number of locules: Two or three
  Green shoulder (before maturity): Absent
  Color at maturity: Red
  Firmness: Firm
  Number of fruits per cluster: 6-8
Disease and Pest Resistances:
  Fusarium wilt (Fusarium oxysporum f. sp. lycopersici) races 1, 2 and 3: Highly resistant
  Tomato yellow leaf curl virus (TYLCV): Highly resistant
  Tomato Spotted Wilt Virus (TSWV): Highly resistant
  Tomato mosaic virus (ToMV): Susceptible
  Alternaria alternata f. sp. lycopersici (Alternaria stem canker, ASC): Highly resistant
  Verticillium wilt (Verticillium albo-atrum and Verticillium dahlia): Highly resistant
  Root-knot nematodes Meloidogyne incognita (Mi), Meloidogyne arenaria (Ma), and Meloidogyne javanica (Mj): Highly resistant Comparison to Other Tomato Varieties Table 3 below compares characteristics of hybrid tomato 'VT19077602' with the tomato variety 'Latino' (unpatented). Column 1 lists the characteristics, column 2 shows the characteristics for hybrid tomato 'VT19077602', and column 3 shows the characteristics for tomato variety 'Latino'.

TABLE 3

| Characteristic | 'VT19077602' | 'Latino' |
|---|---|---|
| Fruit size | Mostly large (130-150 g) | Large (110-140 g) |
| Fruit shape | Obovate | Rectangular or oval blocky |
| Plant health | Very healthy | Healthy |
| Fusarium wilt (Fusarium oxysporum f. sp. lycopersici) races 1, 2 and 3 | Highly resistant | Resistant |
| Tomato mosaic virus (ToMV) | Susceptible | Resistant |
| Tomato yellow leaf curl virus (TYLCV) | Highly resistant | Susceptible |
| Tomato Spotted Wilt Virus (TSWV) | Highly resistant | Susceptible |
| Verticillium wilt (Verticillium alboatrum and Verticillium dahlia) | Highly resistant | Resistant |
| Root-knot nematodes Meloidogyne incognita (Mi), Meloidogyne arenaria (Ma), and Meloidogyne javanica (Mj) | Highly resistant | Susceptible |
| Alternaria alternata f. sp. lycopersici (Alternaria stem canker, ASC) | Highly resistant | Susceptible |

Table 4 below compares characteristics of hybrid tomato 'VT19077602' with the tomato varieties 'SUN 7705' (unpatented) and 'PaiPai' (unpatented) over two separate trials in three years under greenhouse culture in Puebla and San Luis Potosí, Mexico. Column 1 lists the characteristics, columns 2 and 4 show the characteristics for hybrid tomato 'VT19077602', and columns 3 and 5 show the characteristics for tomato varieties 'SUN 7705' and 'PaiPai'. Trial numbers, locations, and evaluation times are noted in row 1, above their respective data.

TABLE 4

| | Trial 1: Huixcolotla, Puebla Evaluation: October, Year 1 | | Trial 2: El Cedral, S.L.P. Evaluation: August, Year 3 | |
|---|---|---|---|---|
| Variety | 'VT19077602' | 'SUN 7705' | 'VT19077602' | 'PaiPai' |
| Days to Harvest | 120 | 120 | — | — |
| Plant Vigor[1] | 3 | 3 | 3 | 4 |
| Disease Pressure[2] | 3 | 3 | 2 | 4 |
| Maturity[3] | Main | Main | Main | Main |
| Yield[4] | 4 | 2 | 4 | 4 |
| Fruit Shape Uniformity[5] | 2 | 2 | 4 | 4 |
| Fruit Size Uniformity[5] | 4 | 2 | 3 | 4 |
| Fruit Size (g) | 130 | 140 | 123 | 127 |
| Fruit Size (cm) | — | — | 7.3 × 6 × 1 | 7.8 × 5.9 × 1 |

[1]Plant Vigor (1-5): 1. No stand/germ.; 2. Poor vigor; 3. Average vigor; 4. Good vigor; 5. Excellent vigor.
[2]Disease Pressure (1-5): 1. No stand/germ.; 2. Poor resistance; 3. Average resistance; 4. Good resistance; 5. Excellent resistance.
[3]Maturity: Relative harvest time compared to other tomato varieties. Categories: Early, Main, Late, Transition.
[4]Yield (1-5): 1. No stand/germ.; 2. Poor yield; 3. Average yield; 4. Good yield; 5. Excellent yield.
[5]Fruit uniformity (1-5): 1. No stand/germ.; 2. Poor uniformity; 3. Average uniformity; 4. Good uniformity; 5. Excellent uniformity.

Further Embodiments

The present disclosure is further directed to methods for producing a tomato plant by crossing a first parent tomato plant with a second parent tomato plant where either the first or second parent tomato plant is a hybrid tomato plant of 'VT19077601' or 'VT19077602'. Further, both first and second parent tomato plants can come from a hybrid tomato plant of 'VT19077601' or 'VT19077602'. All plants produced using a hybrid tomato plant of 'VT19077601' or 'VT19077602' as a parent are within the scope of the disclosure, including plants derived from a hybrid tomato plant of 'VT19077601' or 'VT19077602'. Plants derived from a hybrid tomato plant of 'VT19077601' or 'VT19077602' may be used, in certain embodiments, for the development of new tomato varieties. By selecting plants having one or more desirable traits, a plant derived from a hybrid tomato plant of 'VT19077601' or 'VT19077602' is obtained which possesses some of the desirable traits of the hybrid as well as potentially other selected traits.

The development of new varieties using one or more starting varieties is well known in the art. In accordance with this disclosure, novel varieties may be created by crossing a hybrid tomato plant of 'VT19077601' or 'VT19077602' followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

It is preferred to breed for a combination of desirable plant characteristics and resistances to create a single variety or hybrid containing an improved combination of desirable traits from the parental germplasm. The development of commercial tomato hybrids relates to the development of tomato parental lines, the crossing of these lines, and the evaluation of the crosses. Hybrid varieties offer multiple advantages, including a combination of desirable dominant and recessive traits from a set of inbred parents. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have the desirable characteristics.

Gene Conversions

When the terms "tomato plant", "hybrid", "cultivar", or "tomato line" are used in the context of the present disclosure, this also includes any single gene conversions of that variety. The term single gene converted plant as used herein refers to those tomato plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present disclosure to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental tomato plant that contributes the gene for the desired characteristic is termed the nonrecurrent or donor parent. This terminology refers to the fact that the nonrecurrent parent is used one time in the backcross protocol and therefore does not recur. The parental tomato plant to which the gene or genes from the nonrecurrent parent are transferred is known as the recurrent parent as it is used for several rounds in the backcrossing protocol (Poehlman & Sleper, 1994; Fehr, Principles of Cultivar Development pp. 261-286 (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a tomato plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add an agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Examples of single gene traits include, for example, male sterility, herbicide resistance, resistance for bacterial, fungal, or viral disease, insect resistance, male fertility, enhanced nutritional quality, industrial usage, yield stability, yield enhancement, modified fatty acid metabolism, modified carbohydrate metabolism, and nematode resistance. These genes are generally inherited through the nucleus. Several of these single gene traits are described in U.S. Pat. Nos. 5,959,185; 5,973,234, 5,777,196, 5,948,957, 5,969,212, and 5,977,445.

Tissue Culture

Further reproduction of a tomato variety can occur by tissue culture and regeneration. Tissue culture of various tissues of tomatoes and regeneration of plants therefrom is well known and widely published. It is clear from the literature that the state of the art is such that these methods of obtaining plants are routinely used and have a very high rate of success. Thus, another aspect of this disclosure is to provide cells which upon growth and differentiation produce tomato plants having the physiological and morphological characteristics of a hybrid tomato plant of 'VT19077601' or 'VT19077602'.

As used herein, the term "tissue culture" indicates a composition containing isolated cells of the same or a different type or a collection of such cells organized into parts of a plant. Exemplary types of tissue cultures are protoplasts, calli, plant clumps, meristematic cells, and plant cells that can generate tissue culture that are intact in plants or parts of plants, such as embryos, pollen, flowers, seeds, fruit, petioles, leaves, stems, roots, root tips, anthers, pistils and the like. Means for preparing and maintaining plant tissue culture are well known in the art. By way of example, a tissue culture containing organs has been used to produce regenerated plants. U.S. Pat. Nos. 5,959,185; 5,973,234 and 5,977,445 describe certain techniques.

Vegetative Propagation

Tomato plants can also be propagated vegetatively. Accordingly, the present disclosure is further directed to vegetative propagation of a hybrid tomato plant of 'VT19077601' or 'VT19077602'. A part of the plant, for example a shoot tissue, is collected and a new plant is obtained from the part. Such part typically includes an apical meristem of the plant. The collected part is transferred to a medium allowing development of a plantlet including, for example, rooting or development of shoots, or is grafted onto a tomato plant or a rootstock prepared to support growth of shoot tissue. This is achieved using methods well-known in the art. Accordingly, in one embodiment, a method of vegetatively propagating a tomato plant of the present disclosure involves collecting a part of a plant according to the present disclosure, e.g., a shoot tissue, and obtaining a plantlet from said part. In one embodiment, a method of vegetatively propagating a tomato plant of the present disclosure involves: a) collecting tissue of a plant of the present disclosure; and b) rooting said proliferated shoots to obtain rooted plantlets. In one embodiment, a method of vegetatively propagating a plant of the present disclosure involves: a) collecting tissue of a plant of the present disclosure; b) cultivating said tissue to obtain proliferated shoots; and c) rooting said proliferated shoots to obtain rooted plantlets. In one embodiment, such methods further involve growing a plant from said plantlets. In one embodiment, a fruit is harvested from said plant.

Additional Breeding Methods

The hybrid tomato of the disclosure can also be used for transformation where exogenous genes are introduced and expressed by the cultivar of the disclosure. Genetic variants of 'VT19077601' or 'VT19077602' created either through traditional breeding methods or through transformation of hybrid tomato 'VT19077601' or 'VT19077602' by any of a number of protocols known to those of skill in the art are intended to be within the scope of this disclosure.

Mutations for use in mutation breeding can be induced in plants by using mutagenic chemicals such as ethyl methane sulfonate (EMS), by irradiation of plant material with gamma rays or fast neutrons, or by other means. The resulting nucleotide changes are random, but in a large collection of mutagenized plants the mutations in a gene of interest can be readily identified by using the TILLING (Targeting Induced Local Lesions IN Genomes) method (McCallum et al. (2000) Targeted screening for induced mutations. Nat. Biotechnol. 18, 455-457, and Henikoff et al. (2004) TILLING. Traditional mutagenesis meets functional genomics. Plant Physiol. 135, 630-636). The principle of this method is based on the PCR amplification of the gene of interest from genomic DNA of a large collection of mutagenized plants in the M2 generation. By DNA sequencing or by looking for point mutations using a single-strand specific nuclease, such as the CEL-I nuclease (Till et al. (2004) Mismatch cleavage by single-strand specific nucleases. Nucleic Acids Res. 32, 2632-2641), the individual plants that have a mutation in the gene of interest are identified. By screening many plants, a large collection of mutant alleles is obtained, each giving a different effect on gene expression or enzyme activity. The gene expression or protein levels can for example be tested by transcript analysis levels (e.g., by RT-PCR) or by quantification of protein levels with antibodies. Plants with the desired reduced gene expression or reduced protein expression are then backcrossed or crossed to other breeding lines to transfer only the desired new allele into the background of the crop wanted.

Genes of interest for use in breeding may also be edited using gene editing techniques including transcription activator-like effector nuclease (TALEN) gene editing techniques, clustered Regularly Interspaced Short Palindromic Repeat (CRISPR/Cas9) gene editing techniques, and/or zinc-finger nuclease (ZFN) gene editing techniques. For this, transgenic plants are generated expressing one or more constructs targeting the gene of interest. These constructs may include, without limitation, an anti-sense construct, an optimized small-RNA construct, an inverted repeat construct, a targeting construct, a guide RNA construct, a construct encoding a targeting protein, and/or a combined sense-anti-sense construct, and may work in conjunction with a nuclease, an endonuclease, and/or an enzyme, so as to downregulate the expression of a gene of interest.

One of ordinary skill in the art of plant breeding would know how to evaluate the traits of two plant varieties to determine if there is no significant difference between the two traits expressed by those varieties. For example, see Fehr and Walt, Principles of Cultivar Development, p. 261-286 (1987). Thus the disclosure includes a hybrid tomato plant of 'VT19077601' or 'VT19077602' progeny tomato plants including a combination of at least two 'VT19077601' or 'VT19077602' traits selected from the combination of traits listed in the Overview of the Hybrid 'VT19077601' or 'VT19077602', so that said progeny tomato plant is not significantly different for said traits than a tomato of 'VT19077601' or 'VT19077602', as determined at the 5% significance level when grown in the same environmental conditions and/or may be characterized by percent similarity or identity to a hybrid tomato of 'VT19077601' or 'VT19077602' as determined by SSR markers. Using techniques described herein, molecular markers may be used to identify said progeny plant as a hybrid tomato of 'VT19077601' or 'VT19077602' progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

As used herein, the term "plant" includes plant cells, plant protoplasts, plant cell tissue cultures from which tomato plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

Deposit Information

Hybrid Tomato 'VT19077601'

A deposit of at least 625 seeds of the hybrid tomato variety 'VT19077601' was made with the American Type Culture Collection (ATCC), ATCC Patent Depository, 10801 University Boulevard, Manassas, Virginia, 20110, USA, and assigned ATCC Number PTA-127760. The seeds deposited with the ATCC on May 24, 2024, were obtained from the seed of the variety maintained by VoloAgri Group, Inc., 12050 County Road 97, Woodland, California 95695, USA since prior to the filing date of the application. Access to this deposit will be available during the pendency of this application to persons determined by the Commissioner of Patents and Trademarks to be entitled thereto under 37 C.F.R. § 1.14 and 35 U.S.C. § 122. Upon issuance, the Applicant will make the deposit available to the public consistent with all of the requirements of 37 C.F.R. § 1.801-1.809. This deposit of the hybrid tomato variety 'VT19077601' will be maintained in the ATCC, which is a public depository, for a period of 30 years, or at least 5 years after the most recent request for a sample of the deposit, or for the effective life of the patent, whichever is longer, and will be replaced if it becomes nonviable during that period. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

The invention claimed is:

1. A hybrid tomato seed designated as 'VT19077601', representative sample of seed having been deposited under ATCC Accession Number PTA-127760.

2. A tomato plant produced by growing the seed of claim 1.

3. A plant part from the plant of claim 2, wherein said part is a leaf, a fruit, or a cell.

4. The plant part of claim 3, wherein said part is a fruit.

5. A tomato plant having all of the physiological and morphological characteristics of the tomato plant of claim 2.

6. A plant part from the plant of claim 5, wherein said part is a leaf, a fruit, or a cell.

7. A plant part of claim 6, wherein said part is a fruit.

8. A protoplast produced from the plant of claim 2, wherein said protoplast is produced from a part of the plant selected from the group consisting of root, root tip, meristematic cell, stem, hypocotyl, petiole, cotyledon, leaf, and fruit.

9. A tissue or cell culture produced from protoplasts or cells from the plant of claim 2, wherein said cells or protoplasts are produced from a plant part selected from the group consisting of root, root tip, meristematic cell, stem, hypocotyl, petiole, cotyledon, leaf, and fruit.

10. A tomato plant regenerated from the tissue or cell culture of claim 9, wherein
the plant has all of the morphological and physiological characteristics of a tomato plant produced by growing tomato seed designated as 'VT19077601', representative sample of seed having been deposited under ATCC Accession Number PTA-127760.

11. A method of making tomato seeds, said method comprising crossing the plant of claim 2 with another tomato plant and harvesting seed therefrom.

12. A method of producing a seed derived from the 'VT19077601' tomato plant of claim 2, comprising the steps of:
a) crossing the hybrid tomato designated as 'VT19077601', representative sample of seed having been deposited under ATCC Accession Number PTA-127760, with itself or a second tomato plant; and
b) allowing seed of a 'VT19077601'-derived tomato plant to form.

13. The method of claim 12, further comprising the steps of:
c) crossing a plant grown from 'VT19077601'-derived tomato seed with itself or a second tomato plant to yield additional 'VT19077601'-derived tomato seed;
d) growing the additional 'VT19077601'-derived tomato seed of step (c) to yield additional 'VT19077601'-derived tomato plants; and
e) repeating steps (c) and (d) for an additional 3-10 generations to generate further 'VT19077601'-derived tomato plants.

14. A method of vegetatively propagating a plant of hybrid tomato variety designated as 'VT19077601' the method comprising the steps of:
a) collecting tissue capable of being propagated from a plant of hybrid tomato variety 'VT19077601', representative seed of said hybrid tomato variety having been deposited under ATCC Accession Number PTA-127760;
b) cultivating the tissue to obtain proliferated shoots; and
c) rooting the proliferated shoots to obtain rooted plantlets.

15. The method of claim 14, further comprising step (d) growing plants from the rooted plantlets.

16. A method of producing a tomato fruit, said method comprising growing the plant of claim 2 until it sets at least one fruit, and harvesting the fruit.

* * * * *